(12) United States Patent
Zanghellini (10) Patent No.: US 7,179,083 B2
(45) Date of Patent: Feb. 20, 2007

(54) ORTHODONTIC APPARATUS (76) Inventor: Sergio Zanghellini, via Cavasini 1/B, Samone (TN) (IT) 38050

( * ) Notice: Subject to any disclaimer, the term of this patent is extended or adjusted under 35 U.S.C. 154(b) by 226 days.

(21) Appl. No.: 10/504,475

(22) PCT Filed: Aug. 1, 2003

(86) PCT No.: PCT/IB03/03081

§ 371 (c)(1),
(2), (4) Date: Aug. 12, 2004

(87) PCT Pub. No.: WO2004/014250

PCT Pub. Date: Feb. 19, 2004

(65) Prior Publication Data

US 2005/0130091 A1 Jun. 16, 2005

(30) Foreign Application Priority Data

Aug. 6, 2002 (IT) .......................... TN2002A0014

(51) Int. Cl.
*A61C 7/00* (2006.01)
*B65D 83/10* (2006.01)

(52) U.S. Cl. ............................... 433/4; 433/9; 206/369
(58) Field of Classification Search ..................... 433/4, 433/9; 206/570, 368, 369, 564
See application file for complete search history.

(56) References Cited

U.S. PATENT DOCUMENTS

| 5,007,827 A * | 4/1991 | DiFranco ........................ 433/4 |
| 5,810,582 A * | 9/1998 | Doyle ............................. 433/4 |
| 5,827,058 A * | 10/1998 | Kelly et al. ..................... 433/9 |
| 5,890,892 A * | 4/1999 | Lemchen ........................ 433/9 |

* cited by examiner

*Primary Examiner*—Cris L. Rodriguez
*Assistant Examiner*—Candice C. Stokes
(74) *Attorney, Agent, or Firm*—Alberto Q. Amatong, Jr.; Morris & Amatong, P.

(57) ABSTRACT

An apparatus is provided for applying orthodontic brackets to teeth. The apparatus includes a bracket container having a bracket housing defined therein and a bracket placer positioned relative to the bracket housing to receive a bracket from the bracket container. The bracket housing is configured to house a plurality of brackets. Furthermore, the bracket container includes biased means for biasing brackets in the bracket housing forwardly toward the bracket placer.

57 Claims, 4 Drawing Sheets

ORTHODONTIC APPARATUS

BACKGROUND TO THE INVENTION

The present invention relates to an apparatus for storing, preserving and marketing, in proper hygienic conditions, orthodontic brackets and other consumer materials necessary for the application of orthodontic appliances to the teeth.

Orthodontic appliances are commonly used to align and or rotate the teeth to the correct position. Orthodontic brackets or braces, (hereinafter referred to as brackets), are applied on the teeth to support and direct the necessary corrective force and torque actions. The common procedure to apply the brackets starts with the eroding of each tooth surface on which the brackets will be applied by means of an acid substance. After the relevant time the acid is removed, usually by means of air-water blasts, and then the teeth are ready for application of the brackets. The brackets are applied one at a time and each individual bracket is removed by means of tweezers from a container or the like, in which the brackets are stored loose, so that using the tweezers or the like, each individual bracket has first to be rotated and/or positioned appropriately in order to be grabbed by the tweezers or the like. At this point, using separate glue dispensers or the like, glue is applied to the bracket and then the bracket is applied and properly positioned on the tooth. The same procedure is followed for each individual bracket and once all are applied on all the designated teeth, they are connected together by means of metallic wire or the like provided for the purpose, placing and fixing the wire on the bracket seats to generate the desired corrective force and torque actions on the teeth.

Conventional instruments, however, have their respective drawbacks. Instruments such as tweezers for handling and placing the bracket, air-water syringes for cleaning the tooth's surface, little brushes for applying the acid and the glue, and the like instruments, entail much time, cost and trouble to perform the bracket application, causing much inconvenience to the patient and to both the doctor and his/her assistants. This is mainly due to the manual skills, work effort and low efficiency that are implied with the existing instruments. There is a high risk that a bracket may be accidentally dropped with consequent loss, increased bracket handling, impaired cleanliness and time lost in general.

For example, when a bracket is to be pulled out from the bracket container and applied on the designated tooth, it is difficult to grab, hold and pull out each individual bracket as well as to release and place it on the designated tooth. This occurs as a consequence of having brackets housed within a container or the like with no specific position and orientation and having instruments such as tweezers, bracket containers and the like, which are all separate and individual instruments. In this case, there is the above mentioned risk with the related consequences and also a statement of fact that existing instruments and the like are not user-friendly and do not allow any possible automation of the bracket application on the teeth.

The conventional method is based on a variety of many elementary instruments, and the like as above mentioned, and is also based on many containers, dispensers, and the like, for brackets and consumer materials. This means that, to apply the brackets to the teeth, much time is required and there is also an increased risk of each individual bracket being dropped during the various phases and passages before it is finally applied on the teeth.

SUMMARY OF THE INVENTION

The invention has been made in consideration of the above mentioned problems and is embodied in apparatus to house the brackets and preferably all other consumer materials as are necessary, and to automatically or semi-automatically release brackets from a bracket container and to apply and position them on the teeth with high accuracy, a good degree of reliability and in a low time-consuming fashion.

In order to alleviate the above-mentioned problems, according to a first aspect of the invention there is provided apparatus for applying orthodontic brackets to teeth, including a container for housing said brackets in a predetermined position and/or orientation, a release mechanism for selectively releasing a bracket from the container to a bracket placer for applying the bracket directly to a tooth.

The bracket container is designed to house the brackets, preferably in a set position and orientation so that release of the brackets from the container is facilitated and is more controlled. This is in contrast to prior art in which loose brackets must be individually retrieved from a container causing the problems outlined above. The bracket placer obviates the need for tweezers and other instruments as the apparatus enables a bracket to be automatically or semi-automatically transferred from the container to a tooth without need for a user to arrange the correct position and/or orientation for each bracket.

Preferably, the apparatus further comprises retaining means for retaining the brackets in the container so as to retain the brackets in said predetermined position and/or orientation until they are selectively released from the container. This means that the alignment of the brackets remaining within the container is not disrupted by one of the brackets being released for application to a tooth.

Preferably, said container is loadable with said brackets one by one or, alternatively, by means of a pre-loaded cartridge containing a predetermined number of brackets.

In a preferred form, said release mechanism includes means for isolating one of said brackets from the others, and means for pushing said isolated bracket along a trajectory to reach said bracket placer. In particular, said retaining means can be adapted to simultaneously retain the other brackets, in order to retain them inside the container.

In one embodiment, said release mechanism releases the brackets, in use, sequentially from said container along a substantially linear or a curvilinear trajectory. Advantageously, said container is substantially linear or curvilinear and wherein the brackets are biased forwardly by a spring or the like against the extremities of a first pair of rods so that said brackets are aligned on a substantially linear or curvilinear trajectory and are retained in said predetermined position and/or orientation until selectively released from the container. Furthermore, said release mechanism may include a push button, wherein application of force to the push button causes deformation of said first pair of rods and outward movement of the extremities thereof so as to permit passage of a bracket therethrough. Preferably, said retaining means comprises a second pair of rods on which said push button is mounted and the application of force to the push button causes inward movement of said second pair of rods so as to limit forward movement of the brackets behind the bracket currently being released.

In an alternative embodiment, said release mechanism releases the brackets radially, in use, sequentially from said container. Preferably said container is rotary and each bracket is independently housed in a respective slot (A–J), each bracket being retained in place by the extremities of a pair of rods and retained in said predetermined position and/or orientation until selectively released from the container. Advantageously, said apparatus further comprises a wheel which cooperates, in use, with said container so as to rotate the container in order to align a bracket slot (A–J) with said release mechanism. Further preferably, said release mechanism includes a push button, wherein application of force to the push button causes deformation of one of said pairs of rods and outward movement of the extremities thereof so as to permit passage of a bracket therethrough.

Preferably, said release mechanism and said bracket placer are part of a single device.

In a further preferred form, said container is part of said single device.

Alternatively, said container is separate from said single device. In this embodiment, preferably, the separate container includes means for storing each individual bracket, in an orientation ready for interfacing with said bracket placer, in use, and so that each bracket may be retrieved independently from the container by the bracket placer. Preferably, the brackets can be stored in a matrix formation.

In a preferred form, the apparatus further comprises a glue dispenser device for applying glue components to a bracket surface. Preferably, said glue dispenser device comprises a glue reservoir (18), a watertight piston (17), a nozzle (23) and/or a glue pad (19) and a push button (16) for pushing, in use, the glue through the nozzle (23) and/or the glue pad (19) so as to apply glue to a surface of a bracket (7).

In one embodiment, said glue dispenser device is part of said separate container and whereby, in use, glue can be applied to a bracket automatically upon retrieval of said bracket from the container.

Preferably, the apparatus further comprises a position-adjusting device for adjusting the position and/or orientation of a bracket before applying it to a tooth. In a preferred form, said position-adjusting device comprises at least one spacer (8), which is designed to contact an edge of a tooth so that it is possible to apply a bracket (7) to the tooth at a set distance from the edge of said tooth.

According to a second aspect of the invention, there is provided a container for use in apparatus as described in the preceding paragraphs including means for storing each individual bracket, in an orientation ready for interfacing with said bracket placer, in use, and so that each bracket may be retrieved independently from the container by the bracket placer.

According to a third aspect of the invention, there is provided a disposable bracket applicator kit containing all apparatus necessary for the storage and application of brackets, the apparatus being as described in any of the preceding paragraphs.

According to a fourth aspect of the invention, there is provided a disposable bracket applicator kit including a container for housing said brackets in a predetermined position and/or orientation, a release mechanism for selectively releasing a bracket from the container, a bracket placer for applying the bracket directly to a tooth, and one or more of the following:

a retaining means for retaining the brackets in the container so as to retain the brackets in said predetermined position and/or orientation until they are selectively released from the container;

means for isolating one of said brackets from the others, and means for pushing said isolated bracket along a trajectory to reach said bracket placer;

a glue dispenser device for applying glue components to a bracket surface;

a position-adjusting device for adjusting the position and/or orientation of a bracket before applying it to a tooth.

BRIEF DESCRIPTION OF THE DRAWINGS

These and other objects and features of the present invention will become clear from the following description, given by way of example only and with reference to the accompanying drawings, throughout which like parts are designated by like reference numerals, and in which:

FIG. 3A is a section view of the apparatus of the second embodiment showing the brackets housed in the bracket container and a bracket in the bracket placer device ready to be applied on the tooth.

DESCRIPTION OF THE INVENTION

Hereinafter embodiments of the invention will be described, by way of example, referring to the appended drawings.

An overview of embodiments of the present invention will first be given, before a more detailed description thereof with reference to the accompanying drawings.

The apparatus of the invention is apparatus for applying orthodontic brackets to the teeth, generically referred to below as an "automatic bracket placer". The apparatus is preferably provided with a chassis and a plurality of "devices", hereinafter described in more detail, and which include a "container-dispenser device", a "clamping-releasing device", a "bracket placer device", a "glue dispenser device", a "position adjusting device", and a "cartridge".

The chassis is also the casing of the automatic bracket placer and is designed to house the above-mentioned devices and allow them to work and functionally interface as necessary.

The container-dispenser device houses the brackets, maintaining them in a constant position and orientation so that, when required, they can be easily moved, held, blocked (retained) and released automatically or semi automatically by means of the relevant device. Moreover, the container-dispenser device has a retaining means function to block or retain the brackets so that they constantly maintain the same position and orientation and they cannot inadvertently exit the bracket container. In addition, upon demand, the container-dispenser device allows a repeated automatic or semi-automatic release of brackets to the bracket placer device maintaining constantly the same orientation and position, in a sequence one by one.

The container-dispenser device may be referred to as "linear" in an embodiment where the brackets are housed and released in a sequence from the bracket container along a straight or a curvilinear trajectory. The container-dispenser device may be alternatively referred to as "rotary" in an embodiment where the brackets are housed and radially released. Alternatively the container-dispenser device may be partially linear and/or rotary.

Independently from the fact that the container-dispenser device may be linear, rotary or partially linear and/or rotary, the container-dispenser device may be referred to as "mobile" in an embodiment where the device moves relative to the chassis so that upon activating the clamping-releasing device, the brackets move jointly with the container-dispenser device. Alternatively, the device may be referred to as "fixed" in an embodiment where the device does not move relative to the chassis so that upon activating the clamping-releasing device, the brackets move relative to the container-dispenser device.

The brackets may be loaded one by one into the container-dispenser device or, alternatively, by means of a cartridge pre-loaded with the necessary brackets and intended to be directly plugged into the container-dispenser device or, in an embodiment where the cartridge is used as the container-dispenser device itself, directly into the automatic bracket placer. The cartridge may house the brackets in a linear, rotary, or partially linear and/or rotary manner in accordance to the above definitions for the container-dispenser device.

In an embodiment where the bracket container is a separate part from the automatic bracket placer, the bracket container maintains the same functionalities described above in relation to the container-dispenser device. Therefore, the bracket container houses the brackets maintaining them in a proper position and orientation so that, when requested, they can be easily moved, held, blocked and released automatically or semi-automatically by means of the relevant device. Moreover, when the automatic bracket placer is not in use, the bracket container blocks the brackets so that they constantly maintain the same position and orientation and they cannot move from the bracket container. In addition, when required, the bracket container releases the brackets automatically or semi automatically to devices of the automatic bracket placer such as the bracket placer device hereinafter described, or the like, releasing the brackets with the proper orientation and position, in a sequence one by one any time an input is given to the clamping-releasing device as hereinafter described.

The bracket container may house the brackets in a linear, rotary, or partially linear and/or rotary manner in accordance with the above definitions for the container-dispenser device. In addition the bracket container may be intended and hereinafter mentioned as "patterned" in an embodiment where the brackets are stored in the bracket container in an ordered formation on a surface such as a matrix formation or the like, so that each bracket may be released from the bracket container independently from the others.

Upon receiving an input, the clamping-releasing device releases the brackets from the container-dispenser device in the proper orientation, in a sequence one by one, automatically or semi automatically to the bracket placer device hereinafter described. In the embodiment where the bracket container is a separate part from the automatic bracket placer, this means that the container-dispenser device and the clamping-releasing device are part of the bracket container and the bracket placer device is part of the automatic bracket placer. In any case the clamping-releasing device is designed to isolate one bracket and simultaneously to hold or retain the others so that they cannot inadvertently exit the container-dispenser device or the container. The clamping-releasing device is also designed to push the isolated bracket along a trajectory to reach the bracket placer device with the correct orientation and position.

The input signal may be given for instance by means of a pushing button, a wheel or any other kind of electrical or mechanical switch able to activate the clamping-releasing device by means of finger pressure or an electrical signal. The clamping-releasing device, by means of a barrier, supplies a bracket isolating it from the others so that it may be moved by means of a releasing force or releasing torque acting in order to move the bracket to the bracket placer device. The blocking action, generated by the clamping-releasing device on the other brackets in order to keep them in the container-dispenser device or in the bracket container while the first mentioned bracket is being released, may be obtained for instance by means of the same above mentioned barrier so that it may block the brackets and not let them move or just close the exit of the container-dispenser device or of the bracket container. The barrier is designed to generate an equal and opposite reaction to oppose the releasing force or torque on the brackets which are not to be released. The barrier may also be designed to isolate the brackets from the action of the releasing force or the releasing torque. The term "barrier" is intended to be generic and it may be made of any material suitable for the above mentioned purposes, even including the case where it may be accomplished partially or totally by using one of the brackets. Moreover, to avoid the use of a physical object, the barrier action may be accomplished by means of electromagnetic forces, magnetic forces or equivalent. In addition the barrier may be accomplished by means of combinations of the above-mentioned solutions. The barrier may be fixed or it may be removable and act only when an input is given to the clamping-releasing device. Forces and torques in general, acting upon the given input and operating on the bracket to be supplied and/or on the other brackets being held in the container-dispenser device or in the bracket container, may be generated by means of finger pressure or by means of electrical motors or may be obtained because, upon the given input, elastic deformation energy is released from a component previously pre-compressed or pre-tensioned such as, for instance, springs, elastic materials in general, inflatable components or the like, or by means of pressurized liquid or a gas, or these forces or torques may be generated by means of electromagnetic forces, magnetic forces in general, or these forces and torques may be obtained by means of combinations of the above. Moreover these forces or torques may act directly on the brackets and/or on the barrier or these forces or torques may act indirectly on the brackets and/or on the barrier by means of gearings, cams, pistons, belts, chains, levers, or their combinations or any transmission or drive suitable for this purpose available at the moment from existing technical know how.

The bracket placer device is designed to securely hold the bracket previously received from the clamping-releasing device in order not to allow it to move or in any case not to let it exit the automatic bracket placer until an input is given to the bracket placer device. That input is to allow the bracket placer device to release the bracket from the automatic bracket placer with the proper orientation and position so that the bracket can be correctly applied on the tooth with the correct orientation and position and caused to stay there by means of glue previously applied on the bracket by means of the glue dispenser device hereinafter described. The input signal may be given for instance by means of a pushing button, a wheel or any other electrical or mechanical switch able to activate the bracket placer device by means of finger pressure or an electrical signal. To securely hold the bracket the action of the hereinafter mentioned blocking forces or blocking torques may be used to securely hold and not let the bracket move relative to the bracket placer device itself. The blocking forces and blocking torques in general may be generated by means of finger pressure or by means of electrical motors or may be obtained because an elastic deformation energy is released from a component previously pre compressed or pre-tensioned such as, for instance, springs, elastic materials in general, inflatable components or other equivalents, or by means of a pressurized liquid or gas, or these forces or torques may be generated by means of electromagnetic forces, magnetic forces in general, or these blocking forces and torques may be obtained by means of combinations of the above. Moreover these blocking forces or torques may act directly on the bracket or these forces or torques may act indirectly on the bracket by means of gearings, cams, pistons, belts, chains, levers, or their combinations or other transmission or drive means suitable for this purpose available at the moment from existing technical know how.

The bracket release action from the bracket placer device occurs when an input is given to the bracket placer device in order to stop the action of the blocking forces or torques or in order to activate the hereinafter mentioned relief forces or torques which action is equal and opposite to the blocking forces or torques. The relief forces or torques, acting upon the given input may be generated by means of finger pressure or by means of electrical motors or may be obtained because, upon the given input, an elastic deformation energy is released from a component previously pre-compressed or pretensioned such as, for instance, springs, elastic materials in general, inflatable components or other equivalents, or by means of a pressurized liquid or gas. Alternatively, these forces or torques may be generated by means of electromagnetic forces, magnetic forces in general, or these forces and torques may be obtained by means of combinations of the above. Moreover these relief forces or torques may act directly on the brackets or these forces or torques may act indirectly on the brackets by means of gearings, cams, pistons, belts, chains, levers, or their combinations or other transmission or drive means suitable for this purpose available at the moment from existing technical know how. The action of the blocking forces or torques may be eventually cancelled by means of an obstacle which may be moved to the proper position for this function when the input is given. The obstacle is designed to generate forces and torques equal and against the blocking forces or torques or designed to isolate the bracket from the action of the blocking forces or torques. The term "obstacle" is intended to be generic and it may be made of any material suitable for the above-mentioned purposes, even including the case where it may be accomplished partially or totally by one of the brackets. Moreover, to avoid the use of a physical object, the obstacle action may be accomplished by means of electromagnetic forces, magnetic forces or equivalent. In addition the obstacle may be accomplished by means of combinations of the above-mentioned solutions.

The obstacle may be fixed relative to the chassis and, in this case, the action of the obstacle is always active but when the bracket placer device moves upon the input so as to release the bracket or the obstacle may be removable relative to the chassis so as to have it acting only when an input is given to the bracket placer device by pushing the obstacle into the proper position for this function. To push the obstacle, a pushing force may be used or torques generated by means of finger pressure or by means of electrical motors or may be obtained because upon the given input an elastic deformation energy is released from a component previously pre-compressed or pre-tensioned such as, for instance, springs, elastic materials in general, inflatable components or the like, or by means of a liquid or a gas are put in high or low pressure. Alternatively, these forces or torques may be generated by means of electromagnetic forces, magnetic forces in general, or these forces and torques may be obtained by means of combinations of the above. Moreover these forces or torques may act directly on the obstacle or these forces or torques may act indirectly on the obstacle by means of gearings, cams, pistons, belts, chains, levers, or their combinations or transmission or drive suitable for this purpose available at the moment from the existing technical know how.

The glue dispenser device is designed to apply, upon a given input, all or a part of the glue components onto the relevant bracket surface as are required to affix the bracket on the tooth. While in use, the glue dispenser device, the glue components and the glue containers and dispensers, may be included within and as part of the automatic bracket placer. The glue may be applied for instance by means of pads, each soaked with its own specific glue component, or the glue may be applied by means of nozzles, each one releasing its own specific glue component. The glue components are preserved in suitable conditions, each one in its own container or dispenser and may be released upon an input by pushing these components to the pads or nozzles. This pushing force may be obtained by increasing the pressure in the container by means of a internal volume shrinkage of the container itself. Each glue container may be made in any way so long as it allows such internal volume shrinkage for instance by using elastic or plastic deformable materials as the container material. Alternatively this internal volume shrinkage may be obtained by means of suitable devices such as pistons based on the same principle or by means of suction or introducing into the container a pressurized gas or liquid so to push out each glue component. The internal volume shrinkage may be obtained by means of the action of forces or torques generated themselves by means of finger pressure or by means of electrical motors or may be obtained because upon the given input an elastic deformation energy is released from a component previously pre-compressed or pre-tensioned such as, for instance, springs, elastic materials in general or the like, inflatable components or the like, or by means of a pressurized liquid or gas. Alternatively, these forces or torques may be generated by means of electromagnetic forces, magnetic forces in general, or these forces and torques may be obtained by means of combinations of the above. Moreover these forces or torques may act directly on the glue containers or these forces or torques may act indirectly on the glue containers by means of gearings, cams, pistons, belts, chains, levers, or their combinations or transmission or drive means suitable for this purpose available at the moment from existing technical know how.

The position-adjusting device is designed to easily adjust the position of a bracket as it is being applied on a tooth. This device may act at the same time a bracket is released from the bracket placer device onto the tooth or this device may be used soon after the bracket has been applied on the tooth so as to finally adjust the position and orientation. In any case the purpose of this device is to give the correct bracket orientation and position, for instance by means of a spacer. The device may be in function only when requested, in response to an input or it may be constantly in function.

Moreover the glue dispenser device, the position-adjusting device, and the cartridge may be optional and other additional devices and consumer materials may be included, if desired, for the bracket application on the teeth. When one or more of the above mentioned devices are not used, they may be partially or totally removed from the automatic bracket placer.

In one embodiment of the invention, the automatic bracket placer is pre-packed i.e. already filled with brackets and any other consumer materials which are preserved there in sterile conditions, distributed and marketed with the automatic bracket placer. The automatic bracket placer may be provided sterile and pre-packed with the bracket container already filled with brackets or the bracket container may be refillable with brackets or it may be refillable by means of a sterile pre-packed cartridge containing all necessary brackets. Alternatively, the bracket container may not even be included in the automatic bracket placer and may be supplied as a separate part until finally used for the bracket application so that this results in a faster, precise, practical, hygienic operation, eliminating or highly reducing the risk of dropping the brackets and/or physically manipulating them, thus avoiding the consequent time and bracket loss as well. The automatic bracket placer may be pre packed and already filled with brackets and other consumer materials so that all are provided in a single disposable kit suitable firstly, as a container for brackets, glue and any other consumer materials and so suitable for distributing and marketing such materials and secondly, the automatic bracket placer may be suitable to perform the bracket application. The automatic bracket placer may even be reused more times than intended as refillable, eventually by means of cartridge or cartridges, of brackets and/or any other consumer materials so that each of these cartridges are provided in a single disposable kit suitable firstly, as a container for brackets, glue and any other consumer materials and so suitable for distributing and marketing such materials and secondly, the cartridges may be suitable as refills for the automatic bracket placer for the bracket application.

In accordance with the apparatus and the above described devices, it is possible to have the brackets successively supplied in a sequence, one by one, automatically or semi-automatically from the bracket container, with the proper orientation and position and with glue already applied on them by means of the glue dispenser device. This means that the brackets can be easily and quickly moved from the bracket container to the bracket placer device which is also a part of the automatic bracket placer and securely held there until they are easily and quickly released and applied to the teeth, resulting in a fast and secure bracket application.

In accordance with the apparatus, only one instrument is necessary for both storing and applying the brackets, thus simplifying the procedure. This means that manual handling of the brackets is avoided as well as the use of unnecessary additional instruments. The risk of dropping the brackets is eliminated or highly reduced since they are preserved in sterile conditions in the automatic bracket placer and from there directly applied onto the teeth.

In the embodiment wherein the bracket container is a separate part from the automatic bracket placer, a fast and secure bracket application still results. Only the bracket container and the automatic bracket placer are necessary for both storing and for applying the brackets thus maintaining the above mentioned advantages.

Preferred embodiments of the invention will now be more particularly described, by way of example only, with reference to the accompanying drawings.

First Embodiment

FIGS. 2A, 2B, 2C, 2D and 2E illustrate a first embodiment of the invention.

An apparatus in accordance with the above definition of a "linear" bracket container is accomplished in the first embodiment. The apparatus contains the brackets and consumer materials such as the glue and automatically or semi-automatically releases the brackets from the bracket container and applies and positions then on the teeth with high accuracy, a high degree of reliability and in a non time-consuming manner by means of the hereinafter described devices.

The chassis (1) is also the casing of the automatic bracket placer and is designed to house the devices (described below), allowing them to work and functionally interface as necessary. The chassis (1) includes parts of other devices for which explanation will be given below when the devices are mentioned.

Figure 1A:
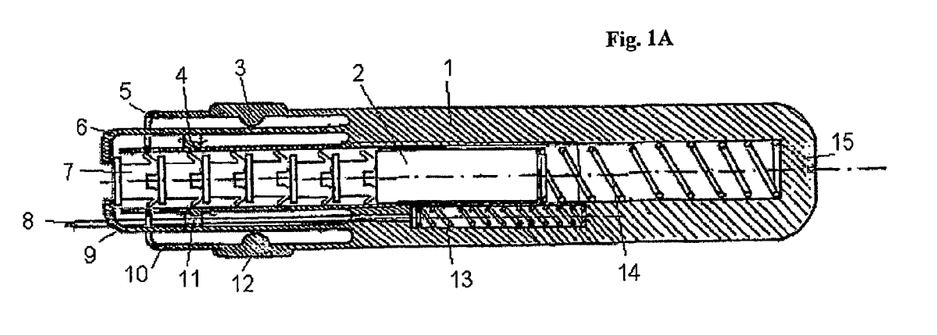
FIG. 1A is a section view of a first embodiment of the apparatus having a linear bracket container and container dispenser device.
Figure 1B:
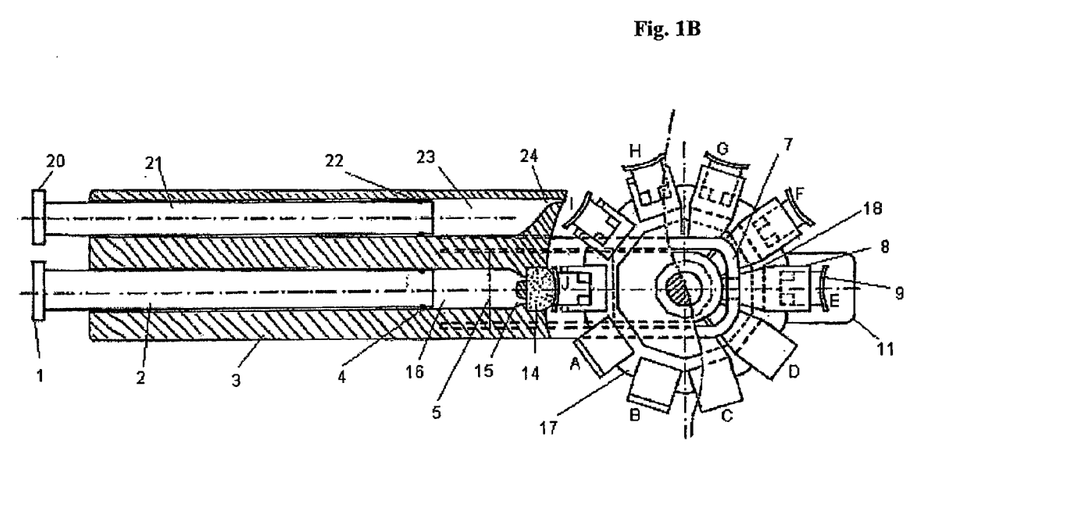
FIG. 1B is a section view of a second embodiment the apparatus having a rotary bracket container and container dispenser device
Figure 2A:
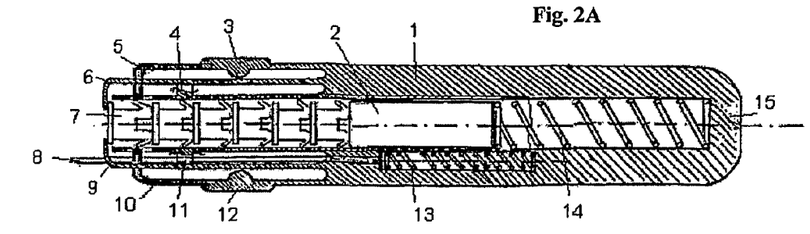
FIG. 2A is a section view of the apparatus of the first embodiment showing the brackets housed in the bracket container and the container-dispenser device.

The container-dispenser device is shown in FIG. 2A and comprises the chassis (1), the rods (6), (9), the piston (2) and the spring (14). This device also serves as the bracket container and it may therefore be noted that, in this embodiment, the container dispenser device includes the bracket container. In accordance with the above definitions, the bracket container and consequently the container-dispense device, is linear and is also fixed. Moreover, the brackets (7) are housed within the container-dispenser device and they cannot exit due to the fact that the chassis (1), as shown in FIG. 2A, allows the brackets to slide only in one direction which is blocked on one side by means of the presence of a barrier made by the rods (6) and (9) and blocked on the opposite side by the compressing action of the piston (2) biased by the spring (14). In this way, the brackets are aligned on a substantially linear trajectory constantly maintaining this position and orientation. In addition, since the brackets (7) are housed in the container-dispenser device with the desired proper orientation and position, they can easily be moved, held, blocked and released automatically or semi-automatically by means of other devices hereinafter described.

Figure 2B:
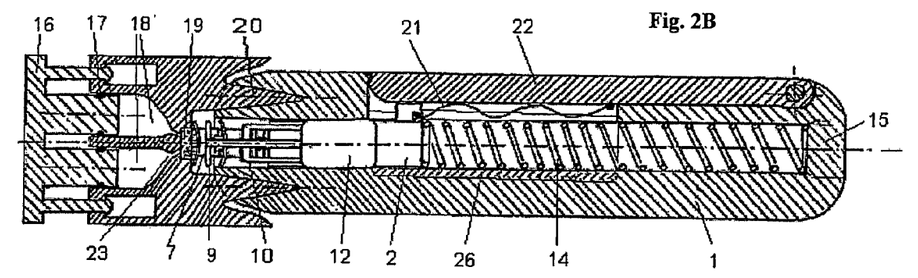
FIG. 2B is a section view orthogonal with respect to the section in FIG. 2A, and including the glue-dispenser device and the clamping releasing device.
Figure 2C:
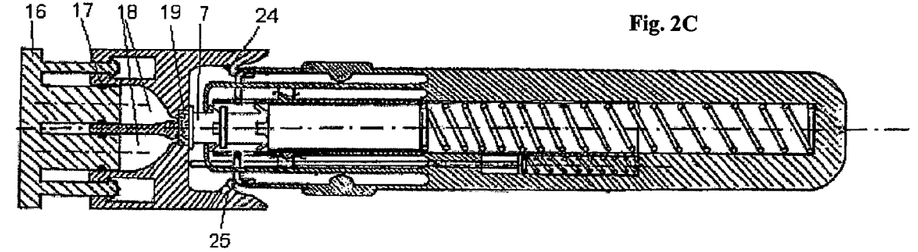
FIG. 2C is a section view orthogonal with respect to the section in FIG. 2B, also including the glue dispenser device and the clamping releasing device.

The clamping-releasing device comprises the push buttons (3) and (12), the rods (5), (6), (9), (10), each with an extreme constrained to the chassis and able to bend, since they are made of elastic material, the fulcrums (4) and (11), the piston (2), the spring (14), the mechanical endstop (19), the aligners (20) and the little hooks (24) and (25). Referring to FIG. 2C and assuming that the brackets are housed in the bracket container as shown in FIG. 2A, it may be noted that giving an input by simultaneously pushing the buttons (3) and (12), the rods (5) and (10) do not interfere on the brackets since these rods, as shown in FIG. 2C, are held by means of the little hooks (24) and (25), and the rods (6) and (9) bend so that their free extremes move away one from each other leaving the bracket to move to the mechanical endstop (19) by means of the pushing action of the piston (2) due to the compressed spring (14) so that a generic bracket (7) always achieves the default position and orientation as shown in FIG. 2C. After that, upon releasing the push buttons (3) and (12), the rods (6) and (9) are allowed to return back to their original position so that these mentioned rods hold and block the bracket as shown in FIG. 2C and, in addition, that above mentioned bracket, does not allow any other bracket housed into the container-dispenser device, to move and exit since that bracket acts as an obstacle which action is against the pushing action of the spring (14). The aligners (20) maintain the alignment and allow the assembly made by the parts (16), (17), (18), (19), (20), (23), (24), (25) to functionally interface with the rest of the automatic bracket placer and to allow this mentioned assembly to be, when it is used, as a single part with the automatic bracket placer. This assembly has to be taken off to physically separate it from the rest of the automatic bracket placer once the clamping-releasing device action is no longer necessary.

Figure 2D:
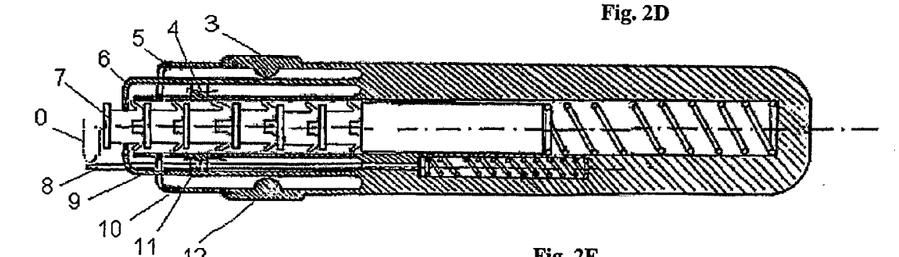
FIG. 2D is a section view of the apparatus of the first embodiment showing the brackets housed in the bracket container and a bracket in the bracket placer device ready to be applied on the tooth.
Figure 2E:
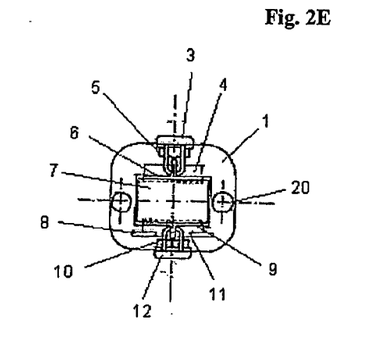
FIG. 2E is a front view of the apparatus of the first embodiment showing a bracket held by the bracket placer device.

In this embodiment, the bracket placer device comprises the push but-tons (3) and (12), the rods (5), (6), (9), (10) each with a constrained extreme to the chassis and able to bend since they are made of elastic material, the fulcrums (4) and (11), the little piston (2) and the spring (14). Referring to FIG. 2D, the bracket (7) is held and blocked by means of the rods (6) and (9) and any other bracket housed into the bracket container maintains the proper position and orientation as long as necessary. As shown in FIG. 2D, it may be also noted that giving an input by simultaneously pushing buttons (3) and (12), the bracket next in position with respect to the one being held and blocked by the rods (6) and (9), is held and blocked by means of the other above mentioned rods (5) and (10). At the same time, the rods (6) and (9) bend so that their free extremes move away one from each other allowing the bracket to be released and be applied onto the tooth (0) by moving the automatic bracket placer back from the tooth, constantly achieving the same orientation and proper position for any bracket release. Moreover, at the same time, the bracket that is held and blocked by the rods (5) and (10), acts as an obstacle not allowing any other bracket to exit the container-dispenser device. After that, releasing the push buttons (3) and (12), the spring (14) pushes the little piston (2) and the remaining brackets against the rods (6) and (9) as shown in FIG. 2A so that it is possible, according to the above description of the devices of the first embodiment, to proceed with the application of the remaining brackets.

In this embodiment, the glue dispenser device includes glue containers (18), watertight pistons (17), nozzles (23), glue pad (19) and a push button (16). As shown in FIG. 2C it may be noted that giving an input by pushing the button (16) the glue is pushed through the nozzles or the glue pad to reach the bracket (7) on the proper surface.

In this embodiment the position-adjusting device includes the chassis (1), the spacers (8) and the spring (13). As shown in FIG. 2D, it may be noted that the spacers (8) are designed to go to contact on the top of the tooth (0) so that it is possible to release the bracket on the tooth at the proper distance from the top of the tooth itself. After that it is possible to use the position-adjusting device for adjusting the bracket into the desired final position. Moreover, it may also be noted that, as shown in FIG. 2C, the position-adjusting device, due to the action of the spring (13), may be pulled back into the chassis (1) by contact of the extreme of the spacer (8) against an object so as not to interfere with it when this device is not used or not necessary and that the position-adjusting device may be deactivated by compressing the spring (13) so that the spacer (8) remains totally inside the automatic bracket placer.

The cartridge (26), housing the brackets, may be plugged into the automatic bracket placer. As shown in FIG. 2B, pulling the hinged rod (22) rotates it so as to pull the cable (21). This action compresses the spring (14) by means of the little piston (2) so that the bracket cartridge slot of the automatic bracket placer can be fully opened and the bracket cartridge can be plugged in. Once the cartridge is plugged in, the rod (22) is rotated back to close the slot and the little piston (2) pushes the brackets by means of the spring (14), so that the brackets are constantly biased in the proper position into the automatic bracket placer and, when requested, they may be easily moved, held and blocked, and released to the other devices as mentioned above. In this case, the cartridge functionally becomes part of the container-dispenser device of the automatic bracket placer as shown in FIGS. 2A, 2B, 2C, and 2D. Also note that for this embodiment the cartridge is linear in accordance to the above given definition.

The necessary brackets may be supplied already housed in the automatic bracket placer ready to be used. Also note that, as described above for the brackets, the automatic bracket placer may even have cartridges for the glue to be plugged-in or it may be supplied with the glue containers already filled up.

The first embodiment accomplishes with the above description, features and advantages of the apparatus given in the summary of the invention.

Furthermore the apparatus may be simplified and reduced in size, conforming with the bracket size, to easily fit into one's hand.

Second Embodiment

FIGS. 3A, 3B, 3C and 3D illustrate a second embodiment of the invention.

An apparatus in accordance to the previous definition of a rotary bracket container is accomplished in the second embodiment hereinafter described and also referred to as an automatic bracket placer. The apparatus contains the brackets and consumer materials such as the glue and automatically or semi-automatically releases the brackets from the bracket container and applies and positions them on the teeth with a high accuracy, degree of reliability and in a low time-consuming manner by means of the hereinafter-described devices.

Figure 3B:
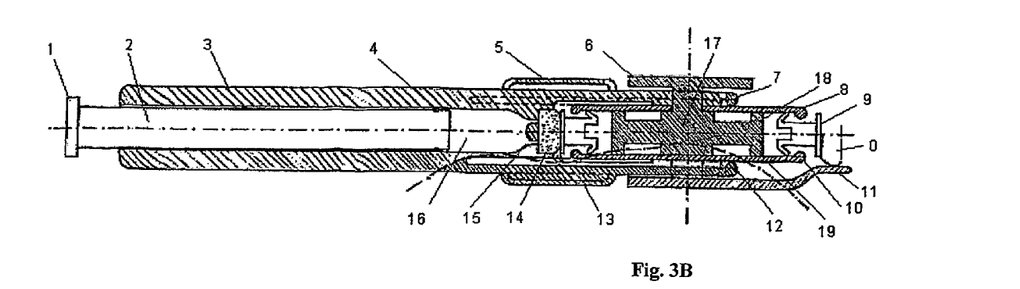
FIG. 3B is a section view orthogonal with respect to the section in FIG. 3A also including the glue dispenser device.

The chassis (3) is also the casing of the automatic bracket placer and is designed to house the devices (described below), allowing them to work and functionally interface as necessary. The chassis (3) includes parts of other devices for which explanation will be given below when the devices are mentioned.

The container dispenser device is shown in FIG. 3B and comprises a chassis (3) and a bracket container (17) which includes also rods (8) and (10) and the like for each one of the bracket slots (A) to (J). FIG. 3B shows also the bracket container function of this device and it may be also noted that the bracket container is included in the automatic bracket placer. In accordance with the above definitions the bracket container and consequently the device, is rotary and the device is also mobile. Moreover, the brackets (9) are housed into the container-dispenser device and they cannot exit since they are each held and blocked into its own bracket slot by means of the rods such as (8) and (10) as is shown in FIGS. 3A and 3B for the bracket slot (E). Moreover the brackets (9) are housed in the container-dispenser device so that they cannot exit due to the holding and blocking action of the rods (8) and (10), and the like for each one of the bracket slots, since each rod has a constrained extreme with respect to the chassis and is able to bend due to the fact that they are made of elastic material in order to create at the other free extreme of the rod a sufficient pressure to hold and block each bracket. Note that the brackets are independently housed in the bracket slots (A) to (J) of the bracket container (17). The brackets, in this way, can be placed radially on a circumference constantly maintaining this position and orientation. In addition, with the brackets (9) housed in the container-dispenser device with the above mentioned proper orientation and position, they can easily be moved, held, blocked and released automatically or semi-automatically by means of other devices hereinafter described.

Figure 3C:
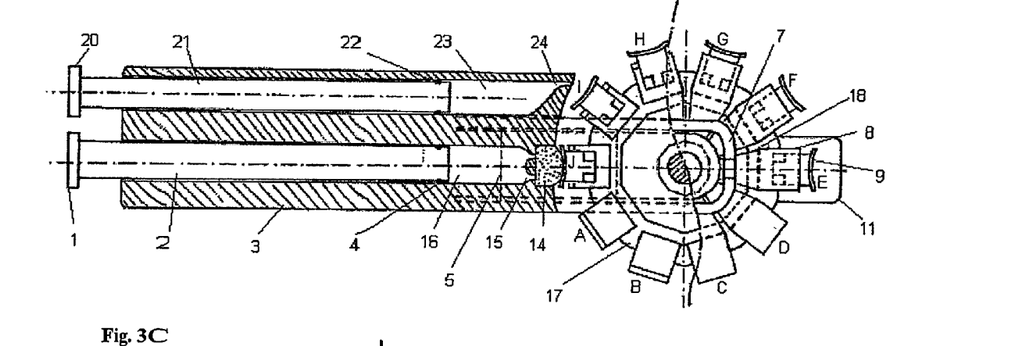
FIG. 3C is a front view of the apparatus of the second embodiment showing a bracket held by the bracket placer device.

The clamping releasing device is accomplished by the small wheel (6) constrained to the bracket container (17) and the container-dispenser device described above for the second embodiment. Referring to FIGS. 3A and 3C, it may be noted that giving an input by rotating the small wheel (6) also jointly rotates the bracket container (17) so that it is possible to align a bracket slot housing its own bracket (9) with the rods (7) and (12) as shown in FIG. 3B for the bracket slot (E). It may be also noted that a bracket in the above mentioned position is already into the bracket placer device hereinafter described.

The bracket placer device is accomplished in the push buttons (5) and (13), the rods (7), (12), (8), (10) each one with a constrained extreme to the chassis and able to bend since they are made of elastic material and the fulcrums (18) and (19). Referring to FIG. 3A, brackets are held and blocked in each bracket slot by means of rods like (8) and (10) so that the brackets maintain the proper position and orientation as long as necessary. As shown in FIG. 3A, it may be also noted that giving an input by simultaneously pushing buttons (5) and (13), the rods (7) and (12) bend, in turn pushing respectively the rods (8) and (10). Moreover, rods (8) and (10) are more elastic than rods (7) and (12) so that they bend in order to move away their free extremes one from each other to allow the bracket to be released and applied on the tooth (0) by moving the automatic bracket placer back from the tooth, constantly achieving the same orientation and proper position for any bracket release. According to the description of the above mentioned devices of the second embodiment, is possible to rotate and align the next bracket slot of the bracket container (17) with the rods (7) and (12) of bracket placer device in order to proceed further with the application of the next bracket and in the same way to proceed further with the application of all the remaining brackets which are in the bracket container. In addition, according to the second embodiment, it may be noted that is possible to independently apply each single bracket by rotating the small wheel (6) to align the chosen bracket slot with the rods (7) and (12) of the bracket placer device.

In this embodiment, the glue dispenser device comprises in the chassis (3), the push buttons (20) and (1), the water tight pistons (21) and (2), the glue containers (16) and (23), the nozzles (24) and (15) and the glue pad (14). As shown in FIG. 3B, it may be noted that by pushing the push button (1), the glue (16) passes through the nozzles (15) and, after that, through the glue pad (14) in order to reach the appropriate surface of the bracket. In addition, upon pushing the push button (20), the glue (23) passes through the nozzle (24) in order to reach the appropriate surface of the bracket. Moreover, it may be noted that the push buttons (1) and (20) may be implemented as just one push button so that it is easier to push both of them at the same time. According to the above-mentioned devices, rotating the small wheel (6) it is possible to apply the glue (16) and (23) respectively on the next brackets. It has to be mentioned that the order for applying the glues depends on their chemical composition. In this embodiment first the glue (16) has to be applied on the proper surface of the bracket and after that the glue (23) before placing the bracket on the tooth.

In this embodiment the position-adjusting device comprises the chassis (3) and the spacer (11) constrained to the chassis (3). As shown in FIG. 3A, the spacer (11) is designed in order to go to contact the top of the tooth (0) so that it is possible to release the bracket on the tooth at the proper distance from the top of the tooth itself. After that it is possible to use the position-adjusting device for subsequently adjusting the bracket to the final position.

The cartridge for the brackets may the bracket container (17) which also includes the rods (8) and (10) and the like, for each one of the bracket slots (A) to (J), in order to house the necessary brackets each in its own bracket slot. In this embodiment, according to the above given definition, the cartridge is rotary. Referring to FIG. 3A and assuming that the above mentioned cartridge is not illustrated in the mentioned figure, it may be noted that the cartridge may be loaded into the automatic bracket placer by sliding it along the axis of the push buttons (1) to the position shown in FIG. 3A and there the cartridge may be constrained to the small wheel (6), which in this case will include a shaft to reach over the other side of the chassis (3), by sliding it along the vertical axis of the cartridge as shown in FIG. 3A. Once the cartridge is plugged in, the brackets are therefore housed in the proper position in the automatic bracket placer and, when desired, they can be easily moved, held and blocked, and released to the other devices as mentioned above. In this case the cartridge functionally becomes part of the container-dispenser device of the automatic bracket placer as shown in FIGS. 3A and 3B.

Figure 3D:
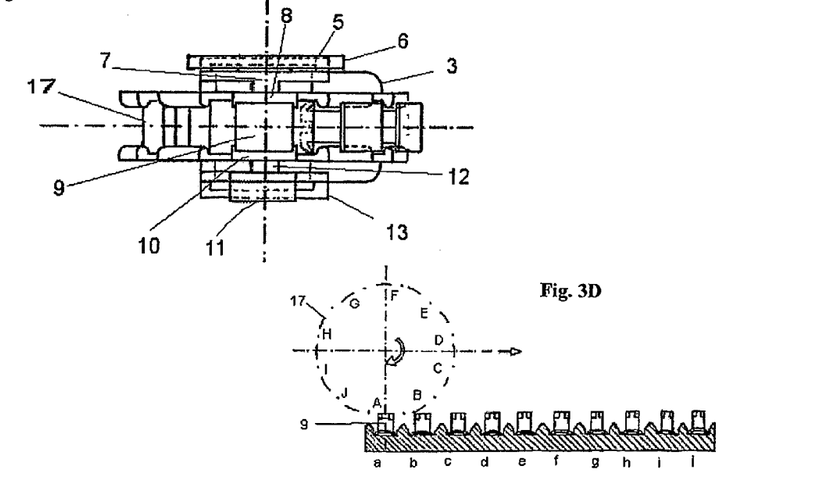
FIG. 3D is a schematic view illustrating a scheme for loading a cartridge for the second embodiment.

An alternative, according to the above given description and definitions in the summary of the invention, the bracket container may be a separate part from the automatic bracket placer and used as a bracket cartridge to load the brackets into the automatic bracket placer as hereinafter described. In addition, as shown in FIG. 3D, it may be noted that, according to the above definitions, the cartridge is patterned and in this case the brackets are placed into the cartridge on a surface and so as to constantly maintain the same position and orientation so that each bracket is available to be independently released from the others. In this embodiment the brackets are housed on a planar surface and linearly placed as shown in FIG. 3D. Referring to the above-mentioned figure, the bracket container (17) can rotate in a synchronized manner keeping in contact with the cartridge which is fixed relative to the bracket container (17). In this way the elastic rods (8) and (10) of the bracket slot (A), bend to clamp, hold and block the bracket into the slot (A) taking it out from the slot (a) of the cartridge where it was before. Continuing to rotate the container (17) the bracket from slot (b) of the cartridge is loaded in the same way into the slot (B) etc. In the same way, bracket-by-bracket, all necessary brackets are loaded until the last one is loaded into the last bracket slot of the container (17) that, in this case, is the slot (J).

The necessary brackets may be supplied already housed in the automatic bracket placer ready to be used. Also note that, as described above for the brackets, the automatic bracket placer may even have cartridges for the glue to be plugged in or it may be supplied with the glue containers already filled up.

The second embodiment accomplishes with the above description, features and advantages of the apparatus which are given in the summary of the invention.

Furthermore the apparatus may be simplified and reduced in size, conforming with the bracket size, to easily fit into one's hand.

Third Embodiment

FIGS. 4A, 4B, 4C and 4D illustrate a third embodiment of the invention.

An apparatus in accordance to the previous given definition of a "patterned" bracket container is accomplished in the third embodiment. In this case the apparatus has two separate parts. The first part, hereinafter also referred to as a container, comprises the bracket container including also the glue containers and the second part, hereinafter also referred to as an automatic bracket placer, comprises all remaining parts of the apparatus. In this embodiment the container contains the brackets and consumer materials such as the glue and tie automatic bracket placer automatically or semi-automatically releases the brackets from the bracket container and applies and positions them on the teeth with a high accuracy, degree of reliability and low time-consuming by means of the hereinafter described devices.

Figure 4A:
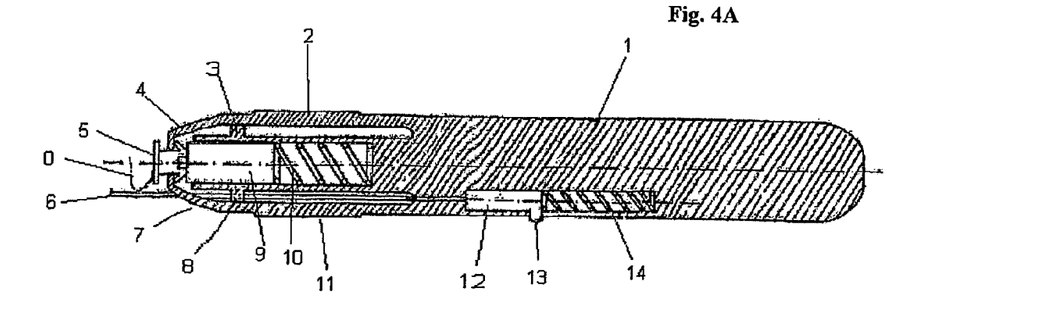
FIG. 4A is a section view of the apparatus of the third embodiment showing the bracket in a bracket placer device ready to be applied on the tooth.
Figure 4B:
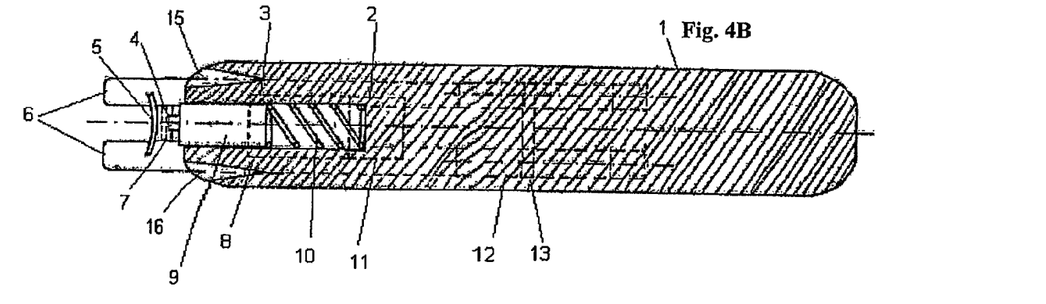
FIG. 4B is a section view orthogonal with respect to the section in FIG. 4A also including the position adjusting device.
Figure 4C:
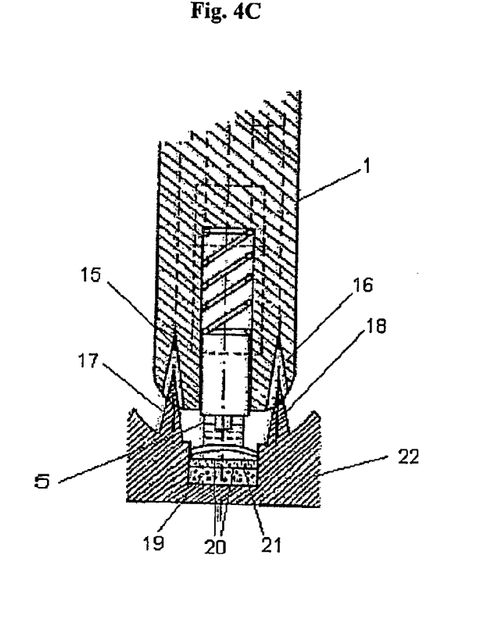
FIG. 4C is a section view of the apparatus of the third embodiment including a patterned bracket container (in which brackets can be stored in an ordered formation, such as a matrix formation) and also showing the glue dispenser device.
Figure 4D:
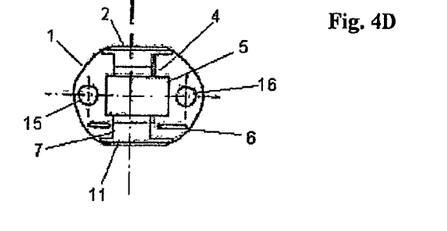
FIG. 4D is a front view of the apparatus of the third embodiment showing a bracket held by the bracket placer device.

The container-dispenser device is accomplished by a generic bracket slot (22) as shown in FIG. 4C and at the same time it is also the bracket container. Moreover, the bracket container is made by as many bracket slots, such as the bracket slot (22) shown in FIG. 4C, as necessary, each one housing its own bracket (5). Each bracket (5) is maintained into the bracket container, constantly held and blocked with the same position and orientation as shown in FIG. 4C, and also maintained in hygienic and sterile conditions isolating the bracket slot from the external environment by means of a removable proper film or cover, which is not shown in FIG. 4C, until the bracket is ready to be released. In addition, according to the above definitions, the container-dispenser device is patterned. It may be noted also that, when desired, the bracket may be pulled out from the bracket container by means of the automatic bracket placer maintaining the proper position and orientation by means of the clamping releasing device hereinafter described.

The clamping releasing device comprises the bracket slot (22) including also the chassis (1), the aligners (15), (16) and the protrusions (17), (18), the piston (9) and the spring (10). Referring to FIG. 4C, the bracket is held and blocked, maintaining constantly and securely the same position and orientation in the above mentioned bracket slot, by means of a mechanical interference between the bracket and the slot in which the bracket is housed. As shown in FIG. 4C, it may also be noted that the bracket slot is shaped in order to create a proper interface with the automatic bracket placer. In this embodiment the aligners (15), (16) of the automatic bracket placer, interface with the protrusions (17), (18) of the bracket slot. Moreover, in this case the interface feature is achieved using a conical geometry but it may be any geometry or shape which allows it to interface and easily align the automatic bracket placer with a bracket slot. Referring to FIG. 4C, it may be noted that, due to the above mentioned interface feature, the rods (4) and (7) touch the bracket (5) simply by plugging the automatic bracket placer into the bracket slot (22) so that, giving an input by pushing the automatic bracket placer, since these rods are made of a proper elastic material and have an extreme constrained to the chassis (1), the rods (4) and (7) bend and follow the bracket profile going to automatically hold and block the bracket as shown in FIG. 4C and in particular in FIG. 4A where it may be noted how the rods (4) and (7) hold and block the bracket (5). Note that, when the automatic bracket placer is plugged into the bracket slot, the bracket (5) pushes the piston (9), which compresses the spring (10). Note also that, as shown in FIG. 4A, the compressed spring (10) pushes the bracket (5), by means of the piston (9), against the extremes of the rods (4) and (7) in order to securely hold and block the bracket. In addition, the piston (9) is blocked at one extreme to the spring (10) and the spring (10) is also blocked at the other extreme to the chassis (1) so that the piston (9) can slide but it cannot leave the automatic bracket placer. Note also that in this embodiment, when the bracket is held and blocked by means of the rods (4) and (7), the bracket is also in the bracket placer device.

In this embodiment the glue dispenser device is shown in FIG. 4C and is accomplished by the bracket slot (22), the watertight compartments (19) and (21) each one containing its own glue component and totally isolated one form the other one by means of a membrane or a film (20). As shown in FIG. 4C, once the bracket is held and blocked by the rods (4) and (7), giving an input by pushing the automatic bracket placer into the bracket slot, the first membrane or film (20) of the glue compartment (21) breaks and releases the glue (21) onto the bracket surface. Upon continuing to push, the other membrane or film (20) of the glue compartment (19) breaks and releases the other glue component (19) onto the bracket surface.

The automatic bracket placer, in this embodiment, is accomplished by the chassis, the bracket placer device and the position adjusting device that are hereinafter described.

The chassis (1) is also the casing of the automatic bracket placer and is designed to house the devices (described below), allowing the m to work and functionally interface as necessary. The chassis ( 1) includes also parts of other devices.

The bracket placer device is accomplished by the chassis (1), the push buttons (2) and (11), the rods (4), (7) each one with a constrained extreme to the chassis and able to bend since are made of elastic material, the fulcrums (3) and (8), the piston (9) and the spring (10). As shown in FIG. 4A, giving an input by pushing at the same time the buttons (2) and (11) the free extremes of the rods (4) and (7) move away one from each other allowing the bracket (5) to be released and be applied on the tooth (0). Note also that the bracket release and application on the tooth is also facilitated by the pushing action of piston (9), obtained by means of the spring (10).

In this embodiment the position adjusting device comprises in the chassis (1), the spring (14), the blocking protrusion (13), the little piston (12) and the spacers (6). As shown in FIG. 4A, it may be noted that the spacers (6) are designed in order to contact the top of the tooth (0) so that the bracket may be released onto the tooth at the proper distance from the top of the tooth itself. After that it is possible to use the position-adjusting device for adjusting the bracket to the final position. Note also that, referring to FIG. 4A, due to the action of the spring (14), the position adjusting device automatically pulls back into the chassis (1) by pushing the top of the spacer (6) against other objects that may interfere with the spacer. In addition, it may be noted that when the position adjusting device is not necessary, it may permanently be pulled back into the automatic bracket placer and stay there as long as necessary by means of the blocking protrusion (13) which engages with holes into the chassis (1) ill order to keep the spacer (6) totally housed in the chassis (1). Once the first bracket is applied on the desired tooth, the next bracket is applied and all others which are necessary.

The necessary brackets may be supplied already housed in the container ready to be used. Also note that, as described for the brackets, the container may even be supplied with the glue containers already filled up.

The third embodiment accomplishes with the above description, features and advantages of the apparatus have been given in the summary of the invention.

Furthermore the apparatus may be simplified and reduced in size, conforming to the bracket size, to easily fit into one's hand.

The foregoing disclosure and description of the invention is illustrative and explanatory thereof. Various changes in the details of the illustrated construction may be made without departing from the scope of the appended claims.

The invention claimed is:

1. An apparatus for applying orthodontic brackets to teeth, said apparatus comprising:
a bracket container having a bracket housing defined therein, said bracket housing being configured to house a plurality of brackets;
a bracket placer positioned relative to said bracket housing to receive a bracket from said bracket container; and
wherein said bracket container includes bias means for biasing brackets in said bracket housing forwardly toward said bracket placer.

2. The apparatus of claim 1, wherein said bracket housing is configured to maintain each of the brackets in said bracket housing in a predetermined orientation.

3. The apparatus of claim 1, further comprising a movable barrier operatively associated with said bracket housing for selectively releasing a bracket from said bracket housing to said bracket placer.

4. The apparatus of claim 1, further comprising a releasing mechanism including a movable barrier positionable into said bracket housing to restrict forwardly passage of a bracket in said bracket housing, said movable barrier being movable to selectively release a bracket from said bracket housing to said bracket placer.

5. The apparatus of claim 1, wherein said bracket container is integrally joined with said bracket placer to form a single device.

6. The apparatus of claim 1, wherein said bracket placer includes a releasing mechanism associated with said bracket housing to selectively release a bracket therefrom and to said bracket placer.

7. The apparatus of claim 1, wherein said bracket container includes a chassis wherein said bracket housing is defined.

8. The apparatus of claim 7, wherein said bracket housing has a substantially linear or curvilinear shape.

9. The apparatus of claim 1, wherein said bracket container is engageable with said bracket placer and rotatable relative therewith to align a bracket for release to said bracket placer.

10. The apparatus of claim 9, wherein said bracket housing includes a plurality of slots each configured to retain a bracket.

11. The apparatus of claim 10, wherein said slots are configured to retain said brackets in a predetermined orientation.

12. The apparatus of claim 1, further comprising a glue dispenser engageable with said bracket container for applying glue to a surface of a bracket retained by said bracket housing.

13. The apparatus of claim 12, wherein said glue dispenser includes a glue reservoir and a nozzle operable to apply glue to a surface of a bracket retained by said bracket housing.

14. The apparatus of claim 13, wherein said glue dispenser is separate from said bracket container and is positionable to apply glue to a bracket automatically upon retrieval of said bracket from the bracket container.

15. The apparatus of claim 1, further comprising a position-adjusting device for adjusting the position of a bracket relative to a tooth before the bracket is applied to the tooth.

16. The apparatus of claim 15, wherein said position-adjusting devices includes a spacer positionable with said bracket placer to contact an edge of the tooth, such that said bracket placer can apply a bracket to the tooth at a set distance from the contact edge.

17. The apparatus of claim 16, wherein said position-adjusting device is formed integrally with said bracket placer.

18. The apparatus of claim 17, wherein said spacer projects, in one position, forwardly of said bracket placer and is retractable therefrom to a second position inwardly of a bracket positioned for placement by said bracket placer.

19. The apparatus of claim 1, wherein said bracket housing is configured to store brackets sequentially therein, said bracket container further comprising bias means engaging brackets in said bracket housing and biasing the brackets forwardly therein toward said bracket placer.

20. The apparatus of claim 19, wherein said bias means includes a spring.

21. The apparatus of claim 19, further comprising a releasing mechanism for selectively releasing individual brackets from said bracket housing said releasing mechanism including a movably moveable barrier engaging the brackets in to resistance to said bias means.

22. An apparatus for applying orthodontic brackets to teeth, said apparatus comprising:
a bracket placer operable to apply an orthodontic bracket to a tooth;
a bracket container operatively engageable with said bracket placer, said bracket container having a bracket housing configured to house a plurality of brackets and positionable relative to said bracket placer to selectively release a bracket to said bracket placer; and a releasing mechanism including a movable barrier positionable into said bracket housing to restrict forwardly passage of a bracket in said bracket housing, said movable barrier being movable to selectively release a bracket from said bracket housing to said bracket placer.

23. The apparatus of claim 22, wherein said bracket housing is configured to house brackets therein in a predetermined orientation.

24. The apparatus of claim 22, further comprising a glue dispenser for applying glue components to a bracket surface, said glue dispenser being engageable with said bracket container to engage brackets in said bracket housing.

25. The apparatus of claim 22, wherein said bracket container is integrally joined with said bracket placer to form a single device.

26. The apparatus of claim 22, wherein said bracket container includes bias means for biasing brackets in said bracket housing forwardly toward said bracket placer.

27. The apparatus of claim 26, wherein said bias means includes a spring.

28. The apparatus of claim 27, wherein said releasing mechanism and said bracket placer are integrally joined to form a single device.

29. The apparatus of claim 28, wherein said bracket container is part of said single device.

30. A container for housing orthodontic brackets, said container comprising:
  a container body having a bracket housing defined therein for housing a plurality of brackets; and
  a releasing mechanism engageable with a bracket in said bracket housing and operable to release a bracket from said bracket housing to a bracket placer engaging said container body.

31. The container of claim 30, wherein said bracket housing is configured to store brackets sequentially therein, said bracket container further comprising bias means engaging brackets in said bracket housing and biasing the brackets forwardly therein toward said bracket placer.

32. The container of claim 30, wherein said releasing mechanism including a movable barrier positionable into said bracket housing to restrict forwardly passage of a bracket in said bracket housing, said movable barrier being movable to selectively release a bracket from said bracket housing to said bracket placer.

33. The container of claim 30, wherein said bracket housing is configured to house each of the brackets in a predetermined orientation.

34. The container of claim 33, wherein said bracket housing is substantially linear or curvilinear.

35. The container of claim 30, wherein said container body is engageable with the bracket placer and rotatable relative therewith to align a bracket for release thereto.

36. The container of claim 35, wherein said bracket housing includes a plurality of slots each configured to retain a bracket.

37. The container of claims 36, wherein each said slot of said bracket housing is configured to operatively engage a bracket placer and release thereto, a bracket oriented in said predetermined orientation.

38. A system for applying orthodontic brackets to teeth, said system comprising:
  a bracket container having a bracket housing defined therein, said bracket housing being configured to house a plurality of brackets;
  a bracket placer engageable with said bracket housing to selectively receive a bracket from said bracket container, wherein said bracket placer is disengageable from said bracket container and operable to apply the received bracket to a tooth; and
  a cartridge engageable with said bracket container to load said bracket container with a consumable material, said cartridae being pre-loadable with consumable products.

39. The system of claim 38, wherein said bracket container including a moveably movable barrier operatively associated with said bracket housing for selectively releasing a bracket from said bracket housing to said bracket placer.

40. The system of claim 38, further comprising a glue dispenser separate from said bracket container and engageable with said bracket container to applying glue to a surface of a bracket retained by said bracket housing.

41. The system of claim 38, wherein said cartridge is preloadable with a plurality of brackets for preloading said bracket housing upon engagement between said bracket containers and said cartridge.

42. The system of claim 41, wherein said cartridge, said bracket container, and said bracket placer are provided in a single disposable package.

43. The system of claim 42, wherein each said cartridge, said bracket container, and said bracket placer includes a distinct identifier matchable wit a plurality consumables or accessories useable therewith,
  wherein the plurality of consumables or accessories include bracket types, glue, and types of position-adjusting devices.

44. A method for applying orthodontic brackets to teeth, said method comprising the steps of:
  providing a bracket container and a bracket placer;
  storing a plurality of orthodontic brackets within the bracket container;
  operating the bracket container to release an orthodontic bracket to a bracket placer;
  utilizing the bracket placer to apply the orthodontic bracket to a tooth; and
  wherein said bracket lacer includes a position-adjusting device, said utilizing step includes the step of adjusting the bracket with the position-adjusting device before applying the bracket to a tooth.

45. The method of claim 44, wherein said storing step includes storing said brackets sequentially in a bracket housing of the bracket container.

46. The method of claim 44, wherein said storing step includes storing said brackets individually in each of a plurality of slots of a bracket housing of the bracket container.

47. The method of claim 44, wherein said utilizing step comprises contacting the edge of a tooth with a spacer to apply a bracket to a tooth at a set distance from the edge of the tooth.

48. The method of claim 44, wherein said storing step includes storing each of the brackets in a bracket housing of the bracket container and each in a predetermined orientation.

49. The method of claim 48, wherein said storing step includes biasing said brackets forwardly in the bracket housing.

50. The method of claim 44, further comprising the steps of operatively engaging the bracket container with the bracket placer prior to said step of operating the bracket container.

51. The method of claim 50, wherein said storing step includes maintaining a bracket in a predetermined orientation corresponding with the orientation of the bracket placer such that, upon said operating step, the bracket is directly received by the bracket placer and retained therein in the same predetermined orientation.

52. The method of claim 50, further comprising the steps of:
providing a glue dispenser; and
engaging the bracket container with the glue dispenser, prior to the step of engaging the bracket container with the bracket placer, to apply glue to a surface of a bracket retained in the bracket housing, such that the bracket released in said releasing step has glue applied thereon.

53. The method of claim 52, wherein the bracket container includes a movable barrier operatively associated with the bracket housing for selectively releasing a bracket from the bracket housing to the bracket placer, said releasing step including operating the bracket container to move the movable barrier from the bracket housing and permit passage of a bracket from the bracket container to the bracket placer.

54. A disposable bracket applicator kit comprising a container for housing said brackets in a predetermined position and/or orientation;
a release mechanism for selectively releasing a bracket from the container;
a bracket placer for applying the bracket directly to a tooth; and
a retaining means for retaining the brackets in the container so as to retain the brackets in said predetermined position and/or orientation until they are selectively released from the container.

55. The kit of claim 54, further comprising means for isolating one of said brackets from the others, and means for pushing said isolated bracket along a trajectory to reach said bracket placer.

56. The kit of claim 55 further comprising a glue dispenser device for applying glue components to a bracket surface; and
a position-adjusting device for adjusting the position and/or orientation of a bracket before applying it to a tooth.

57. The kit of claim 56, further comprising a package containing each of said container, said release mechanism, said bracket placer, said retaining means, said glue dispenser, and said position-adjusting device, wherein said package and contents provide a single disposable kit.

\* \* \* \* \*